US008792701B2

(12) United States Patent
Djeridane et al.

(10) Patent No.: US 8,792,701 B2
(45) Date of Patent: Jul. 29, 2014

(54) METHOD FOR ESTIMATING HAEOMODYNAMIC PARAMETERS BY JOINT ESTIMATION OF THE PARAMETERS OF A GLOBAL PERFUSION MODEL

(75) Inventors: Fayçal Djeridane, Marseilles (FR); Fabrice Pautot, La Ciotat (FR)

(73) Assignee: Olea Medical, La Ciotat (FR)

( * ) Notice: Subject to any disclaimer, the term of this patent is extended or adjusted under 35 U.S.C. 154(b) by 199 days.

(21) Appl. No.: 13/376,245

(22) PCT Filed: Jun. 1, 2010

(86) PCT No.: PCT/FR2010/051068
§ 371 (c)(1),
(2), (4) Date: Feb. 21, 2012

(87) PCT Pub. No.: WO2010/139895
PCT Pub. Date: Dec. 9, 2010

(65) Prior Publication Data
US 2012/0141005 A1       Jun. 7, 2012

Related U.S. Application Data

(60) Provisional application No. 61/213,417, filed on Jun. 5, 2009, provisional application No. 61/259,268, filed on Nov. 9, 2009.

(30) Foreign Application Priority Data

Nov. 30, 2009   (FR) ...................................... 09 05759

(51) Int. Cl.
*G06K 9/00* (2006.01)
(52) U.S. Cl.
USPC ....................................................... 382/131

(58) Field of Classification Search
None
See application file for complete search history.

(56) References Cited

U.S. PATENT DOCUMENTS 3,789,832 A * 2/1974 Damadian ..................... 600/410

OTHER PUBLICATIONS

Joshua S. Shimony et al., Estimation of Cerebral Blood Flow From Dynamic Susceptibility Contrast MRI Using a Tissue Model, AIP Conference Proceedings, American Institute of Physics, New York, vol. 803, Aug. 7, 2005, pp. 535-542.
Vonken E.P.A. et al., Maximum Likelihood Estimation of Cerebral Blood Flow in Dynamic Susceptibility Contrast MRI, Magnetic Resonance in Medicine, vol. 41, No. 2, Jan. 1, 1999, pp. 343-350.
Brunecker et al., Correcting saturation effects of the arterial input function in dynamic susceptibility contrast-enhanced MRI—a Monte Carlo simulation, Magnetic Resonance Imaging, vol. 25, No. 9, Oct. 25, 2007, pp. 1300-1311.

(Continued)

*Primary Examiner* — Bhavesh Mehta
*Assistant Examiner* — Siamak Harandi
(74) *Attorney, Agent, or Firm* — Buchanan Ingersoll & Rooney PC

(57) ABSTRACT

The invention relates to a method for estimating haemodynamic perfusion parameters of an elementary volume—termed a voxel—of an organ, from perfusion signals by jointly estimating the parameters of an optionally limited comprehensive perfusion model. The invention moreover relates to a processing unit of a perfusion imaging analysis system, adapted for carrying out such a method and for delivering the estimated parameters according to an appropriate format to a human-machine interface able to represent said estimated parameters for a user.

23 Claims, 5 Drawing Sheets

(56) References Cited

OTHER PUBLICATIONS

Kim et al., Multiphasic contrast injection for improved precision of parameter estimates in functional CT, Med. Phys. vol. 35, No. 12, Dec. 2008, pp. 5921-5933.

K.A. Miles et al., Perfusion CT: a worthwhile enhancement?, The British Journal of Radiology, vol. 76, Apr. 2003, pp. 220-231.

K. Mouridsen et al., Bayesian estimation of cerebral perfusion using a physiological model of microvasculature, Neuroimage, Academic Press, Orlando, FL, vol. 33, No. 2, Nov. 1, 2006, pp. 570-579.

Thomas Benner et al., Accuracy of Gamma-Variate Fits to Concentration-Time Curves from Dynamic Susceptibility-Contrast Enhanced MRI: Influence of Time Resolution, Maximal Signal Drop and Signal-to-Noise, Magnetic Resonance Imaging, vol. 15, No. 3, pp. 307-317, 1997.

\* cited by examiner

METHOD FOR ESTIMATING HAEOMODYNAMIC PARAMETERS BY JOINT ESTIMATION OF THE PARAMETERS OF A GLOBAL PERFUSION MODEL

The invention concerns a system and method for estimating one or more haemodynamic perfusion parameters. The invention is based in particular on Perfusion Weighted Magnetic Resonance Imaging (PW-MRI) techniques or Computed Tomography (CT). These techniques make it possible to quickly obtain precious information on the haemodynamics of organs such as the brain or heart. This information is particularly crucial for a practitioner seeking to establish a diagnosis and to make a therapeutic decision in the emergency treatment of pathologies such as strokes.

In order to implement such techniques, use is made of a nuclear magnetic resonance imaging apparatus or computed tomography apparatus. This delivers a plurality of sequences of digital images of a part of the body, in particular of the brain. The said apparatus applies for this purpose a combination of electromagnetic waves at high frequency on the part of the body in question and measures the signal re-emitted by certain atoms. The apparatus thus makes it possible to determine the chemical composition and therefore the nature of the biological tissues at each point (or voxel) of the volume imaged.

Image sequences are analysed by means of a dedicated processing unit. This treatment unit in the end delivers to a practitioner an estimation of the haemodynamic parameters from the perfusion images, by means of a suitable human-machine interface. The practitioner can thus make a diagnosis and decide on the therapeutic action that he judges suitable.

Nuclear magnetic resonance perfusion or computed tomography images are obtained by injecting a contrast agent (for example a gadolinium salt for magnetic resonance imaging) intravenously and recording its bolus over the course of time at each voxel of the image. For reasons of concision, the indices x, y, z for identifying the voxels will be omitted. For example, instead of denoting as $S_{x,y,z}(t)$ the signal for a voxel of coordinates x, y, z, it will be denoted simply S(t). It will be understood that the operations and calculations described hereinafter are generally performed for each voxel of interest, so as to obtain in the end images or maps representing the haemodynamic parameters that it is sought to estimate.

A standard model makes it possible to connect the intensity of the signals S(t) measured over a time t, at the concentration C(t) of the said contrast agent.

For example, in perfusion computed tomography, the signal for each voxel is directly proportional to the concentration: $S(t)=\alpha \cdot C(t)$, $\alpha$ being a non-zero constant.

In nuclear magnetic resonance perfusion imaging, there exists an exponential relationship $S(t)=S_0 \cdot e^{-k \cdot TE \cdot C(t)}$ where $S_0$ is the mean intensity of the signal before the arrival of the contrast agent, TE the echo time and k is a constant dependent on the relationship between the paramagnetic susceptibility and the concentration of the contrast agent in the tissue. The value of the constant k for each voxel being unknown, this is fixed at an arbitrary value for all the voxels of interest. In this way relative rather than absolute estimations are obtained. The said relative information remains relevant since the concern is mainly with the variation in these relative values in space.

The concentration C(t) can then be expressed itself by the standard perfusion convolution model $C(t)=BF \cdot C_a(t) \otimes R(t)$ where $C_a(t)$ is the concentration of the contrast agent in the artery supplying the tissue volume in a voxel (Arterial Input Function—AIF), BF is the blood flow in the tissue volume, R(t) is the residue function of the transit time in the tissue volume and $\otimes$ designates the convolution product.

Starting from an experimental signal S(t), known methods consist of estimating first of all $S_0$ by taking for example its mean before the contrast agent arrives. In this way an estimation is obtained of the concentration of the contrast agent C(t) by means of the equation $$C(t) = -\frac{1}{k \cdot TE} \ln\left[\frac{S(t)}{S_0}\right].$$

Knowing C(t) and the arterial input function $C_a(t)$, it is then possible to obtain, by digital deconvolution, the function BF·R(t) under the standard perfusion model.

Subsequently, it is possible to obtain an estimation of the parameter BF since R(0)=1 by definition. In addition an estimation of the mean transit time in the tissue is obtained, since $$MTT = \int_0^{+\infty} R(t) dt.$$

It is also possible to obtain an estimation of the blood volume (BV) in the tissue by means of the equation BV=BF·MTT.

According to the prior art, it does not appear to be possible to design a processing unit able to implement a method for deconvolution of the standard perfusion model $C(t)=BF \cdot C_a(t) \otimes R(t)$ without needing to provide an arterial input function $C_a(t)$. This because the said model is expressed in the form of a single equation and there exist two unknowns.

Techniques have therefore been envisaged for fixing one or more arterial input functions $C_a(t)$ and thus make possible the deconvolution of concentration curves C(t) in order to estimate the haemodynamic parameters.

To estimate haemodynamic parameters of an organ such as the human brain, according to a first technique, a global arterial input function is chosen manually by a practitioner. The choice may relate for example to the sylvian artery contralateral to the pathological hemisphere in the case of perfusion imaging of the brain. It is possible to obtain as a variant a global arterial input function by means of supplementary measurements, for example optical.

Though it makes it possible to obtain signals with high signal to noise ratios, this technique nevertheless causes numerous drawbacks. First of all, it requires human intervention and/or additional measurements. This may be highly detrimental in an emergency clinical situation. In addition, the procedures and the final results are difficult to reproduce. Next and especially, the global arterial input function does not correspond to the local arterial input functions for the tissues of interest. It differs in terms of delay since the local arterial input functions are usually late compared with the global arterial input function taken upstream. It also differs in terms of dispersion since the propagation of the contrast agent is slower downstream than upstream. However, it is known that such phenomena have a considerable influence on the estimations of the haemodynamic parameters. In particular, according to this first technique, an estimation of the true mean transit time MTT between the local arterial input function and the venous output function is not obtained. There is obtained only a mean transit time between the global arterial input function and venous output function. In order to attempt to quantify these clashes with respect to the standard perfusion model, some have introduced new description parameters, such as a parameter TMAX=argmaxR(t), even though the said parameters do not intervene in the standard perfusion model. Other methods tend to minimise the influence of these clashes on the estimation of the haemodynamic parameters but introduce new unknowns in the global problem.

According to a second technique a global arterial input function is obtained automatically from perfusion images by means of signal processing techniques such as data partitioning (clustering) or independent component analysis (ICA). This second technique dispenses with human intervention. However, this approach does not solve the problems of delay and dispersion inherent in global arterial input functions.

According to a third approach, local arterial input functions are produced automatically from perfusion images by means of signal processing techniques and selection criteria. For example, the "best" function in the immediate vicinity of the current voxel for which it is wished to estimate the haemodynamic parameters is sought. The purpose of this third technique is to obtain in the end estimations that are less biased and more precise. Problems of delay and dispersion are, at least partly, dispensed with. However, nothing guarantees a priori and a posteriori that the local arterial input functions thus obtained are relevant approximations of the "true local function" for the voxel of interest. For example, this "true" function might not be situated in the vicinity in question if the latter is too small. The said "true" function could also be confused with another arterial input function if the vicinity in question is too large. Consequently, even if the results can be better than with a global arterial input function, the uncertainties weighing on the local arterial input functions (and consequently on the haemodynamic parameters) remain to major extent.

Whatever the technique employed up until then the deconvolution of the concentration curve by the arterial input function, whether this be global or local (and consequently the estimation of the haemodynamic parameters) is performed using, for example, non-parametric deconvolution methods such as singular value decomposition, Hunt deconvolution in the frequency domain, Tikhonov regularisation, etc.

Methods using parametric and semiparametric physiological models $C_a(t,\Theta_a)$ for the arterial input function and $R(t,\Theta_R)$ for the complementary cumulative distribution function of the transit time in the tissue, have however been proposed in the literatures. The purpose of the known use of such models is not to supplant the deconvolution operation but to attempt to improve certain results obtained by the non-parametric methods as described previously.

For example, a parametric physiological model $C_a(t,\Theta_a)$ of the local arterial input function, a "mono-Gamma" model, has one component and four parameters $$\begin{cases} C_a(t, \Theta_a) = \dfrac{a(t-t_0)^{\alpha_0-1} e^{-(t-t_0)/\beta_0}}{\beta_0^{\alpha_0} \Gamma(\alpha_0)} \\ \Theta_a = (a, \alpha_0, \beta_0, t_0) \\ \Gamma(\ )\text{Euler gamma function} \end{cases}$$

This kind of model was introduced in order to:
synthesise simulation data for studying and validating the non-parametric deconvolution methods;
reducing the measurement noise and smoothing the data by replacing the experimental arterial input functions with an adjustment of these smooth models to the said curves before effecting the numerical deconvolution and estimation of the parameters;
overcoming the problems related to the time sampling of the arterial input functions by artificially oversampling an adjustment of these models to the said curves before effecting the numerical deconvolution;
overcoming the problems due to the phenomenon of recirculation of the contrast agent in the voxel of interest, when it overlaps in time the first passage of the contrast agent.

Likewise, parametric or semiparametric models $R(t,\Theta_R)$ of the complementary cumulative distribution function of the transit time in the tissue, have been proposed, among which can be cited:

the "box-shaped" parametric model:

$$\begin{cases} R(t, \Theta_R) = \chi_{[0, MTT]}(t) \; t \geq 0 \\ \Theta_R = MTT \\ \chi_E(\ ) \text{ indicator function} \end{cases}$$

the "triangle" parametric model:

$$\begin{cases} R(t, \Theta_R) = \left(1 - \dfrac{t}{2 \cdot MTT}\right) \chi_{[0, 2 \cdot MTT]}(t) \; t \geq 0 \\ \Theta_R = MTT \\ \chi_E(\ ) \text{ indicator function} \end{cases}$$

the "monoexponential" parametric model:

$$\begin{cases} R(t, \Theta_R) = e^{-\frac{t}{MTT}} \; t \geq 0 \\ \Theta_R = MTT \end{cases}$$

the two-parameter "integral gamma" parametric mode:

$$\begin{cases} R(t, \Theta_R) = \int\limits_{t}^{+\infty} h(\tau, \alpha, \beta) d\tau \; t \geq 0 \\ h(\tau, \alpha, \beta) = \dfrac{t^{\alpha-1} e^{-t/\beta}}{\beta^\alpha \Gamma(\alpha)} \; \alpha > 0, \beta > 0 \\ \Theta_R = (\alpha, \beta) \\ \Gamma(\ ) \text{ Euler gamma function} \end{cases}$$

These models were introduced in order to:
synthesise simulation data for study and validation of the non-parametric deconvolution methods; this is for example the case with the "box-shaped" and "triangle" models, which represent extreme cases that may not be encountered in nature;
obtain, reciprocally by adjustment of these models to the experimental data, complementary cumulative distribution functions of the transit time in the tissue R(t) that are more "physiological" than those obtained by the non-parametric methods (in particular, functions that are positive, decreasing and equal to one at time t=0, as defined under the standard perfusion model);
analytically obtain other functions and parameters of interest dependent on the complementary cumulative distribution function, such as the probability density function h(t) of the transit time in the tissue (pulse response) given by $$h(t) = \delta(t) - \frac{dR(t)}{dt}$$

where $\delta(t)$ is Dirac generalised function.

The use of such models has made it possible to improve more or less certain estimations of parameters. However, the drawbacks inherent in the fact of fixing the arterial input function, whether this be global or local, remain present.

The invention makes it possible to respond to all the drawbacks raised by the known solutions. It offers rapid, objective and reproducible procedures. The invention does not relate to a diagnosis method as such since a method according to the invention does not encompass all the steps allowing such a diagnosis. In particular, the invention does not concern investigation phases allowing collection of data performed for example by means of a nuclear magnetic resonance imaging apparatus. The invention also does not concern steps of interaction with a human or animal body enabling a practitioner to perform a diagnosis.

However, the advantages afforded by the invention are numerous and significant. The invention may prove to be particularly appreciated in an emergency clinical situation, thus offering to a practitioner an aid for perfecting a diagnosis and making an appropriate therapeutic decision.

Implementation of the invention also enables a researcher to progress in the physical understanding of an organ of a human or animal.

Among the many advantages, the following can be mentioned:
- elimination of any human intervention and/or additional experimental measures for attempting to choose, manually or automatically, a global arterial input function or local arterial input functions;
- obtaining estimations of the haemodynamic parameters of interest that are less biased and more precise while dispensing with deconvolution problems that are "badly posed" and numerically unstable as well as by construction, problems of delay and dispersion inherent in the global or local arterial input functions approaches;
- optionally supplying estimations of the local arterial input functions as well as complementary cumulative distribution functions for each tissue voxel in order for example to compare and validate the contribution of the invention compared with the prior art;
- optionally supplying confidence intervals on the estimation of each of the parameters and even bets on the said confidence intervals;
- optionally providing a quantitative and objective measurement of the goodness-of-fit of the global perfusion model to the experimental data and consequently allowing comparison and selection of the most suitable models.

To this end, a method is provided for estimating one or more haemodynamic perfusion parameters of an elementary volume—referred to as a voxel—of an organ, the said method being implemented by a processing unit of a perfusion imaging analysis system, and comprising a step for estimating one or more haemodynamic parameters from perfusion signals S(t), characterised in that the step for estimating the haemodynamic parameter or parameters consists of a joint estimation of the parameters Θ of a global perfusion model comprising:
- a first relationship between the perfusion signal S(t) and a concentration C(t) of a contrast agent circulating in the said voxel over a time t;
- a second relationship between the concentration C(t) of a contrast agent, the blood flow BF, a parametric or semi-parametric model $C_a(t,\Theta_a)$ of an arterial input function and a parametric or semiparametric model $R(t,\Theta_R)$ of a complementary cumulative distribution function of the transit time in the voxel, $\Theta_a$ and $\Theta_R$ being respectively the parameters of the said models $C_a(t,\Theta_a)$ and $R(t,\Theta_R)$.

According to a first example of an application of the invention, such a method may relate to:
- a perfusion signal S(t) previously obtained from digital images delivered by a magnetic resonance perfusion imaging apparatus;
- a global perfusion model wherein:
  - the first relationship can be expressed by $S(t)=S_0 e^{-k \cdot TE \cdot C(t)}$ where $S_0$ is the mean intensity of the signal before the arrival of the contrast agent in the voxel, TE is an echo time and k is a non-zero constant;
  - the second relationship can be expressed by $C(t)= \eta \cdot BF \cdot C_a(t,\Theta_a) \otimes R(t,\Theta_R)$ where $\otimes$ designates the convolution product, $\eta$ is a non-zero constant and BF is the blood flow circulating in the voxel in question.

According to a second example of an application of the invention, such a method may relate to:
- a perfusion signal S(t) previously obtained from digital images delivered by a computed tomography perfusion imaging apparatus;
- a global perfusion model wherein:
  - the first relationship may be a proportionality equation $S(t)=\alpha \cdot C(t)$ where $\alpha$ is a non-zero constant;
  - the second relationship can be expressed by $C(t)= \eta \cdot BF \cdot C_a(t,\Theta_a) \otimes R(t,\Theta_R)$ where $\otimes$ designates the convolution product, $\eta$ is a non-zero constant and BF is the blood flow circulating in the voxel in question.

According to a first embodiment, a method according to the invention can be implemented by successive iterations for a plurality of voxels in question.

By way of example, the joint estimation of the parameters Θ of the global perfusion model implemented by the processing unit may be performed by means of the Bayes method or the method of maximum likelihood or the method of non-linear least squares.

According to a preferred embodiment, the method can comprise a step for quantifying the goodness-of-fit of the global perfusion model to experimental perfusion data $D=[S(t_1), \ldots, S(t_N)]$ by a calculation of a probability $$p(D \mid M) = \int_\Theta p(\Theta \mid M) p(D \mid \Theta, M) d\Theta$$

of these data given the said model.

Provision may also be made for the method according to the invention to be able to comprise a prior step for choosing a global perfusion model from a plurality.

Thus it is possible for such a method to be able to be implemented iteratively by the processing unit for each global perfusion model known from the said processing unit.

According to the preferred embodiment previously described, provision may then be made for the estimated parameters according to the perfusion model to be delivered, the probability of which, given the data, is the greatest.

Apart from an estimation of one or more haemodynamic parameters, the invention provides for the method to be able to comprise a step for calculating supplementary information in the form of:

an estimated arterial input function $C_a(t, \widehat{\Theta_a})$;

an estimated complementary cumulative distribution function $R(t, \widehat{\Theta_R})$;

a confidence interval associated with a parameter of the global perfusion model;

or a bet associated with a parameter of the global perfusion model.

The invention provides an embodiment of the method so that it can comprise a step for delivering estimated haemodynamic parameters, or even all other supplementary information that would be associated therewith, to a human-machine interface able to restore the said estimated parameters to a user.

The invention also provides a variant according to which the global perfusion model comprises a third relationship $\Psi(\Theta_a)=0$ between the parameters $\Theta_a$ of the model of the arterial input function $C_a(t,\Theta_a)$.

The invention also concerns a processing unit comprising storage means, means for communicating with the outside world and processing means, so that:

the means for communicating are able to receive from the outside world a signal S(t) obtained by perfusion imaging;

the storage means comprise a global perfusion model, the said model comprising:

a first relationship between the perfusion signal S(t) and a concentration C(t) of a contrast agent circulating in said voxel in the course of the time t;

a second relationship between the concentration C(t), the blood flow BF, a parametric or semiparametic model $C_a(t,\Theta_a)$ of an arterial input function and a parametric or semiparametric model $R(t,\Theta_R)$ of a complementary cumulative distribution function of the transit time in the voxel, $\Theta_a$ and $\Theta_R$ being respectively the parameters of the said models;

the processing means are adapted to implement a method for estimating haemodynamic perfusion parameters according to the invention.

The invention concerns a variant of a processing unit the means for communicating of which are able to receive from the outside world digital perfusion images from which the processing means determine a perfusion signal S(t) and implement a method for estimating one or more haemodynamic perfusion methods according to the invention.

The invention also provides for the communication means of a processing unit according to the invention to be able to deliver an estimated parameter according to an appropriate format to a human-machine interface able to restore the said estimated parameter to a user.

The invention also concerns any perfusion imaging analysis system comprising a processing unit as described above and a human-machine interface able to restore to a user one or more estimated parameters according to a method in accordance with the invention and implemented by the said processing unit.

Other features and advantages will emerge more clearly from a reading of the following description and an examination of the figures that accompany it, among which:

FIGS. 1 and 2 present two variant embodiments of a perfusion imaging analysis system;

FIGS. 3 and 4 present respectively a perfusion image obtained by a nuclear magnetic resonance imaging apparatus, and a slice of a human brain with the injection of a contrast agent and during the circulation thereof in the tissues of the said brain;

FIGS. 5*a* and 5*b* present a typical nuclear magnetic resonance perfusion signal S(t) relating to a voxel of a human brain;

FIG. 6 presents a typical concentration curve C(t) of a contrast agent circulating in a voxel of a human brain;

FIG. 7 presents a typical arterial input function $C_a(t)$;

FIG. 8 presents a method according to the invention;

FIGS. 9 to 14 present respectively a map relating to an estimated haemodynamic parameter according to the invention;

FIGS. 15 and 16 concern respectively standard deviations of the blood flows and mean transit time estimated in accordance with the invention;

FIG. 17 concerns a map relating to a probability that a cerebral blood flow is in a confidence range.

FIG. 1 presents a perfusion image analysis system. An apparatus 1 for imaging by nuclear magnetic resonance or computed tomography is controlled by means of a console 2. A user can thus choose parameters 11 for controlling the apparatus 1. From information 10 produced by the apparatus 1, a plurality of sequences of digital images 12 of a part of a body of a human or animal are obtained. By way of preferred example, we illustrate the solutions issuing from the prior art as well as the invention by means of digital images issuing from the observation of a human brain. Other organs could also be considered.

The image sequences 12 could optionally be stored in a server 3 and constitute a medical case 13 of a patient. Such a case 13 can comprises images of different types, such as perfusion or diffusion images. The image sequences 12 are analysed by means of a dedicated processing unit 4. The said processing unit comprises means for communicating with the outside world in order to collect the images. The said means for communicating also enable the processing unit to in the end deliver to a practitioner 6 or to a researcher an estimation of the haemodynamic parameters from the perfusion images 12, by means of an adapted human-machine interface 5. The user 6 of the analysis system can then confirm or invalidate a diagnosis, decide on a therapeutic action that he deems appropriate, go deeper into research work, etc. Optionally, this user can parameterise the functioning of the processing unit 4 by means of parameters 16. For example, he may thus define display thresholds or choose the estimated parameters that he wishes to display.

FIG. 2 illustrates a variant embodiment of an analysis system for which a pre-processing unit 7 analyses image sequences 12 in order to derive therefrom perfusion signals 15 per voxel. The processing unit 4 responsible for estimating the haemodynamic parameters 14 is thus relieved of this action and uses a method of estimation from perfusion signals 15 received its means in order to communicate with the outside world.

FIG. 3 illustrates an example of a typical image 12 of a slice 5 millimeters thick of a human brain. This image is obtained by nuclear magnetic resonance. By means of this technique it is possible to obtain, for each slice, a matrix of 128×128 voxels, the dimensions of which are 1.5×1.5×5 millimeters. By means of a bilinear interpolation it is possible to produce a flat image of 458×458 pixels such as the image 20.

FIG. 4 illustrates an image 20 similar to the one presented in relation to FIG. 3. However, this image is obtained after injection of a contrast agent. This image is an example of a typical perfusion image of a brain. The arteries thus appear clearly unlike the same image described in FIG. 3. According to known techniques, it is possible to choose one or more arterial input functions 21 in the hemisphere contralateral to the pathological hemisphere in order to estimate haemodynamic parameters.

FIG. 5b illustrates an example of a nuclear magnetic resonance perfusion signal S(t) such as the signals 15 delivered by the pre-processing unit 7 described in relation to FIG. 2. The perfusion signal thus represents the change in a voxel in the course of time t following an injection of a contrast agent. By way of example, FIG. 5b describes such a signal over a period of 50 seconds. The Y axis describes the intensity of the signal, the unit of which is arbitrary. To obtain such a signal, the processing unit 4 according to FIG. 1 (or in a variant the pre-processing unit 7 according to FIG. 2) analyses a sequence of n nuclear magnetic resonance perfusion images $I1, I2, \ldots, Ii, \ldots, In$ at instants $t_1, t_2, \ldots, t_i, \ldots, t_n$ as described for example by FIG. 5a. For a given voxel, for example for the voxel V, a perfusion signal S(t) representing the change in the voxel in the course of time t following an injection of a contrast agent.

FIG. 6 presents a concentration curve derived from a perfusion signal such as the one described in FIG. 5b. As already mentioned previously, there exists a relationship between the perfusion signal and an associated concentration curve. Thus, in nuclear magnetic resonance perfusion imaging, there exists an exponential relationship $S(t) = S_0 \cdot e^{-k \cdot TE \cdot C(t)}$ where $S_0$ is the mean intensity of the signal before the arrival of the contrast agent, TE is the echo time and k is a constant dependent on the relationship between the paramagnetic susceptibility and the concentration of the contrast agent in the tissue. The value of the constant k for each voxel being unknown, it is fixed at an arbitrary value for all the voxels of interest.

FIG. 6 thus displays, over the course of time, the change in the concentration of a contrast agent in a voxel. A high-amplitude peak is noted during the first pass of the contrast agent in the voxel followed by lower-amplitude peaks related to a recirculation phenomenon (the second pass) of the said contrast agent.

As for FIG. 7, this illustrates a typical arterial input function $C_a(t)$ representing the circulation of a contrast agent in an arterial voxel such as the voxel 21 presented in relation to FIG. 4. FIG. 7 shows in particular that the recirculation phenomenon after a first pass of the contrast agent is very weak.

To implement the invention, a parametric or semi-parametric physiological model $C_a(t, \Theta_a)$ of an arterial input function is introduced. Such a model is stored by storage means or programmed in the processing unit 4 of an analysis system as described in relation to FIGS. 1 and 2.

According to a preferred embodiment of the invention, this model is a so-called "tri-gamma" model with twelve parameters, defined by:

$$\begin{cases} C_a(t, \Theta_a) = \frac{a(t-t_0)^{\alpha_0-1} e^{-(t-t_0)/\beta_0}}{\beta_0^{\alpha_0} \Gamma(\alpha_0)} + \frac{b(t-t_1)^{\alpha_1-1} e^{-(t-t_1)/\beta_1}}{\beta_1^{\alpha_1} \Gamma(\alpha_1)} + \\ \qquad \frac{c(t-t_2)^{\alpha_2-1} e^{-(t-t_2)/\beta_2}}{\beta_2^{\alpha_2} \Gamma(\alpha_2)} \\ \Theta_a = (a, b, c, \alpha_0, \beta_0, t_0, \alpha_1, \beta_1, t_1, \alpha_2, \beta_2, t_2) \\ \Gamma(\,): \text{Euler gamma function} \end{cases}$$

In addition, a parametric or semi-parametric physiological model $R(t, \Theta_R)$ of the complementary cumulative distribution function of the transit time in the tissue is introduced.

In the same way as the arterial input function model, such a model is stored or programmed in the processing unit 4 of an analysis system as described in relation to FIG. 1 or 2.

By way of example, this complementary cumulative distribution function of the transit time may be a so-called "corrected integral gamma" model with two parameters:

$$\begin{cases} R(t, \Theta_R) = H(t) - \int_0^t h(\tau, MTT, \beta) d\tau \\ h(\tau, MTT, \beta) = \frac{t^{\frac{MTT}{\beta}-1} e^{-t/\beta}}{\beta^{\frac{MTT}{\beta}} \Gamma\left(\frac{MTT}{\beta}\right)} MTT > 0, \beta > 0 \\ \Theta_R = (MTT, \beta) \\ H(\,): \text{generalised Heaviside step function} \\ \Gamma(\,): \text{Euler gamma function} \end{cases}$$

By introducing only parametric or semi-parametric models for the arterial input function and for the complementary cumulative distribution function, the invention makes it possible to obtain very satisfactory results. However, the invention provides a variant for which the precision of the estimation obtained is particularly improved. This is because a standard perfusion model, for example in nuclear magnetic resonance imaging, may be expressed in the following equivalent manner:

$$M: \begin{cases} S(t) = S_0 e^{-k \cdot TE \cdot C(t)} \\ C(t) = (\lambda \cdot BF) \frac{C_a(t, \Theta_a)}{\lambda} \otimes R(t, \Theta_R) \end{cases}$$

$\lambda$ being a non-zero constant.

Thus, if $\widehat{BF}$ and $\widehat{C_a(t, \Theta_a)}$ are two estimations fitting the theoretical perfusion model to the experimental data, then $\lambda \widehat{BF}$ and $$\frac{\widehat{C_a(t, \Theta_a)}}{\lambda}$$

are two other estimations fitting the model just as well to the experimental data for any $\lambda \neq 0$.

In other words, BF and $C_a(t, \Theta_a)$ are determined only to within a multiplicative constant under a standard perfusion model. The Bayes method in particular does however make it possible to obtain satisfactory results since it makes it possible to take account of information where a priori there are available the manipulative quantities that make certain values of said quantities, in particular BF and $C_a(t, \Theta_a)$, more probable. Consequently some values of the multiplying constant $\lambda$ are themselves more probable, which has the effect of making the problem of estimating the quantities better determined.

However, to make this problem perfectly determined and thus to improve the precision of the estimation of parameters such as BF or $\Theta_a$, the invention makes provision for introducing an additional constraint $\Psi(\Theta_a)$ on the model of the arterial input function $C_a(t, \Theta_a)$. This third relationship can express for example the preservation of a physical quantity on all of the arterial input functions of interest, such as the total mass of contrast agent circulating in an arterial voxel over time.

Particularly advantageously, this constraint is independent of the model $C_a(t,\Theta_a)$ in question.

This constraint may be expressed, in general terms, by a relationship between the parameters $\Theta_a$ of the model of the arterial input function such as $\Psi(\Theta_a)=0$.

This additional relationship in the form of a constraint on the model of the arterial input function $C_a(t\Theta_a)$ makes it possible to fix, once and for all and for all the voxels in question, the constant $\lambda$. This third relationship is stored or programmed in the processing unit 4 of an analysis system as described in relation to FIG. 1 or 2. The set of three relationships constitute a constrained global perfusion model.

The problem of the joint estimation of the parameters $\Theta$ of the constrained global model, in particular BF and $\Theta a$, then becomes entirely well determined and posed.

According to a first embodiment of the invention, this constrain $\Psi(\Theta_a)=0$ can be expressed as:

$$\int_0^{+\infty} C_a(t,\Theta_a)\,dt = C_0$$

where $C_0$ is an non-zero arbitrary constant identical for all the voxels of interest.

In the case of the "tri-gamma" model for an arterial input function of parameters $\Theta_a=(a,b,c,\alpha_0,\beta_0,t_0,\alpha_1,t_1,\alpha_2,\beta_2,t_2)$, this constraint on the parameters can be expressed as $a+b+c=C_0$.

This therefore gives the equation: $\Psi(\Theta_a)=a+b+c-C_0$.

Under this constraint, it is thus possible to eliminate one of the three parameters, for example c by posing $c=C_0-a-b$, and come down to a constrained model $C_a(t,\Theta_a)$ with eleven free parameters such that:

$$\begin{cases} C_a(t,\Theta_a) = \dfrac{a(t-t_0)^{\alpha_0-1}e^{-(t-t_0)/\beta_0}}{\beta_0^{\alpha_0}\Gamma(\alpha_0)} + \dfrac{b(t-t_1)^{\alpha_1-1}e^{-(t-t_1)/\beta_1}}{\beta_1^{\alpha_1}\Gamma(\alpha_1)} + \\ \qquad\qquad \dfrac{(C_0-a-b)(t-t_2)^{\alpha_2-1}e^{-(t-t_2)/\beta_2}}{\beta_2^{\alpha_2}\Gamma(\alpha_2)} \\ \Theta_a = (a,b,c,\alpha_0,\beta_0,t_0,\alpha_1,\beta_1,t_1,\alpha_2,\beta_2,t_2) \\ \Gamma(\ )\ \text{Euber gamma function} \end{cases}$$

According to a second embodiment, the constraint can be expressed as $$\int_0^{+\infty} C_{ca}(t,\Theta_{ca})\,dt = C_0$$

where $C_{ca}(t,\Theta_{ca})$ is a component of the model $C_a(t,\Theta_a)$ modelling the concentration of the contrast agent during its first pass and $C_0$ is a non-zero arbitrary constant identical for all the voxels of interest.

In the case of the "tri-gamma" model, this component is simply the first of its three components:

$$\begin{cases} C_{ca}(t,\Theta_{ca}) = \dfrac{a(t-t_0)^{\alpha_0-1}e^{-(t-t_0)/\beta_0}}{\beta_0^{\alpha_0}\Gamma(\alpha_0)} \\ \Theta_{ca} = \{a,\alpha_0,\beta_0,t_0\} \end{cases}$$

so that the constraint becomes $a=C_0$ that is to say $\Psi(\Theta_a)=a-C_0$.

This can therefore once again amount to a constrained model $C_a(t,\Theta_a)$ with eleven free Parameters such that:

$$\begin{cases} C_a(t,\Theta_a) = \dfrac{C_0(t-t_0)^{\alpha_0-1}e^{-(t-t_0)/\beta_0}}{\beta_0^{\alpha_0}\Gamma(\alpha_0)} + \dfrac{b(t-t_1)^{\alpha_1-1}e^{-(t-t_1)/\beta_1}}{\beta_1^{\alpha_1}\Gamma(\alpha_1)} + \\ \qquad\qquad \dfrac{c(t-t_2)^{\alpha_2-1}e^{-(t-t_2)/\beta_2}}{\beta_2^{\alpha_2}\Gamma(\alpha_2)} \\ \Theta_a = (b,c,\alpha_0,\beta_0,t_0,\alpha_1,\beta_1,t_1,\alpha_2,\beta_2,t_2) \\ \Gamma(\ )\ \text{Euler gamma function} \end{cases}$$

The invention thus makes it possible to amount to a problem of joint estimation of the parameters $\Theta=(\Theta_a,\Theta_R,BF,S_0,\Theta_B)$ in magnetic resonance imaging or $\Theta=(\Theta_a,\Theta_R,BF,\Theta_B)$ in computed tomography, where $\Theta_B$ is a parameter vector characterising the measurement noise on the perfusion signal $S(t)$, without having to previously supply or estimate any arterial input function.

The invention is thus based on a constrained model, possibly constrained, comprising:
- a first relationship between a perfusion signal $S(t)$ and a concentration $C(t)$ of a contrast agent circulating in a tissue voxel over the course of time t;
- a second relationship between the said concentration $C(t)$, the blood flow BF, a parametric or semi-parametric model $C_a(t,\Theta_a)$ of an arterial input function and a parametric or semi-parametric model $R(t,\Theta_R)$ of a complementary cumulative distribution function of the transit time in the voxel, $\Theta_a$ and $\Theta_R$ being respectively the parameters of the said models;
- optionally, a third relationship $\Psi(\Theta_a)=0$ between the parameters $\Theta_a$ of the model of the arterial input function $C_a(t,\Theta_a)$.

It will be possible to consider the models respectively of an arterial input function $C_a(t,\Theta_a)$ and of a complementary cumulative distribution function of the transit time $R(t,\Theta_R)$ to be sub-models of a global perfusion model optionally constrained by the said third relationship $\Psi(\Theta_a)=0$ between the parameters $\Theta_a$ of the said model of the arterial input function $C_a(t,\Theta_a)$.

By way of example in nuclear magnetic resonance imagining, such a global constrained perfusion model M can be expressed in a form such that:

$$M:\begin{cases} S(t) = S_0 e^{-k\cdot TE\cdot C(t)} \\ C(t) = \eta\cdot BF\cdot C_a(t,\Theta_a)\otimes R(t,\Theta_R) \\ \Psi(\Theta_a)=0 \\ \Theta = (\Theta_a,\Theta_R,BF,S_0,\Theta_B) \end{cases}$$

where $\otimes$ designates the convolution product, $\eta$ is an arbitrarily fixed non-zero constant and BF is the blood flow circulating in the voxel in question.

Likewise, in computed tomography imaging a global constrained perfusion model M can be expressed in a form such that:

$$M:\begin{cases} S(t) = \alpha\cdot C(t) \\ C(t) = \eta\cdot BF\cdot C_a(t,\Theta_a)\otimes R(t,\Theta_R) \\ \Psi(\Theta_a)=0 \\ \Theta = (\Theta_a,\Theta_R,BF,\Theta_B) \end{cases}$$

where $\otimes$ designates the convolution product, $\eta$ is an arbitrarily fixed non-zero constant, BF is the blood flow circulating in the voxel in question and a non-zero constant.

In relation to FIG. 8, a method for estimating haemodynamic parameters in accordance with the invention comprises a step 51 for jointly estimating the parameters Θ of a model M from perfusion signals S(t). Such a method is used by a processing unit 4, as described in FIG. 1 or 2, adapted to be able in particular to use mathematical and numerical techniques for solving a problem of joint estimation of parameters.

By way of examples, such a processing unit 4 is able to use the method of maximum likelihood methods, the method of non-linear least squares methods or Bayes method.

In order to illustrate a preferred embodiment of the invention, we will consider that:
- the processing unit 4 uses the Bayes method;
- the arterial input function model stored or programmed in the processing unit 4 is the "tri-gamma" model;
- the complementary cumulative distribution function model stored or programmed in the processing unit 4 is the "corrected integral gamma" model;
- the constraint stored or programmed in the processing unit 4 is $\Psi(\Theta_a) = C_0 - a - b - c$.

For a nuclear magnetic resonance perfusion imaging application, the constrained model $C_a(t, \Theta_a)$ is therefore written:

$$\begin{cases} C_a(t, \Theta_a) = \frac{a(t-t_0)^{\alpha_0-1} e^{-(t-t_0)/\beta_0}}{\beta_0^{\alpha_0} \Gamma(\alpha_0)} + \frac{b(t-t_1)^{\alpha_1-1} e^{-(t-t_1)/\beta_1}}{\beta_1^{\alpha_1} \Gamma(\alpha_1)} + \\ \qquad \frac{(C_0-a-b)(t-t_2)^{\alpha_2-1} e^{-(t-t_2)/\beta_2}}{\beta_2^{\alpha_2} \Gamma(\alpha_2)} \\ \Theta_a = (a, b, \alpha_0, \beta_0, t_0, \alpha_1, \beta_1, t_1, \alpha_2, \beta_2, t_2) \\ \Gamma(\,) \text{ Euler gamma function} \end{cases}$$

Let $t_i$, i=1,N be the sampling instants and $S(t_i)$, i=1,N the intensity of the perfusion signal measured at these instants. The experimental data are therefore $D = [S(t_1), \ldots, S(t_N)]$.

If a white, stationary, additive Gaussian noise of standard deviation $\sigma = \Theta_B$ is assumed and, then the likelihood function or direct probability distribution of the perfusion data D, given all the parameters, is written:

$$p(D \mid \Theta, M) = (2\pi)^{-\frac{N}{2}} \sigma^{-N} e^{-\frac{\sum_{i=1}^{N} [S(t_i) - S_0 e^{-k \cdot TE \cdot C(t_i)}]^2}{2\sigma^2}}$$

$C(t) = \eta \cdot BF \cdot C_a(t, \Theta_a) \otimes R(t, \Theta_R)$ is calculated numerically after temporal discretisation or preferably analytically using an approximation for the convolution product of two probability distributions Γ.

Given a prior joint probability distribution of all the parameters given the model p(Θ|M) representing the information available before the experiment on these parameters, an a posteriori joint distribution is obtained by means of the Bayes rule:

$$p(\Theta \mid D, M) = \frac{p(\Theta \mid M) p(D \mid \Theta, M)}{\int_{\Theta} p(\Theta \mid M) p(D \mid \Theta, M) d\Theta} \propto p(\Theta \mid M) p(D \mid \Theta, M)$$

From this joint distribution, the method according to the invention makes it possible to obtain 52 the marginal a posteriori distribution of each of the haemodynamic parameters of interest θ such as the blood flow BF⁻, the blood volume BV or the mean transit time MTT, marginalising all the others. From this marginal distribution, it is finally possible to obtain an estimator of the parameter, for example the Bayes estimator under the quadratic loss function taking the mathematical expectation of this distribution or the most probable value of the parameter (the maximum a posteriori estimator). Thus the invention makes it possible for example to be able to estimate, for any voxel of interest, the blood flow $\widehat{CBF}$ in an organ, an estimation of the blood volume $\widehat{CBV}$ and an estimation of the mean transit time $\widehat{MTT}$.

Optionally, a method according to the invention makes it possible to obtain 52a supplementary information in the form of confidence intervals on estimated parameters and even bets 52b on the said confidence intervals. This supplementary information may be particularly useful, for a user such as a practitioner, and prove to be an additional aid in developing a diagnosis. Using techniques of the art prior to the invention, a practitioner has no idea of the precision of the estimations available to him for each voxel of interest.

For example, for a particular haemodynamic parameter θ, such as the cerebral blood flow θ=CBF, the invention makes it possible to obtain an a posteriori marginal distribution:

$$p(\theta \mid D, M) = \int_{\Theta \setminus \theta} p(\Theta \mid D, M) d(\Theta \setminus \theta)$$

and then a Bayes estimator $\hat{\theta}$ of θ under the quadratic loss function $L(\theta - \hat{\theta}^Q) = (\theta - \hat{\theta}^Q)^2$:

$$\hat{\theta}^Q = \int_{\theta} \theta \cdot p(\theta \mid D, M) d\theta$$

or the most probable value of the parameter:

$$\hat{\theta}^P = \operatorname*{argmax}_{\theta} p(\theta \mid D, M)$$

The unit 4 can also optionally deduce:
the variance of the Bayes estimator under the quadratic loss function:

$$\hat{\sigma}^2 \theta = \int_{\theta} (\theta - \hat{\theta}^Q)^2 \cdot p(\theta \mid D, M) d\theta$$

a confidence interval, for example the confidence interval at ±1σ:

$$[\hat{\theta} - \hat{\sigma}\theta, \hat{\theta} + \hat{\sigma}\theta]$$

According to one embodiment, the processing unit 4 using a method according to the invention makes it possible to calculate 52b a probability or bet that the parameter is in the confidence interval, for example:

$$p(\theta \in [\hat{\theta} - \hat{\sigma}_\theta, \hat{\theta} + \hat{\sigma}_\theta]) = \int_{\hat{\theta} - \hat{\sigma}\theta}^{\hat{\theta} + \hat{\sigma}\theta} p(\theta \mid D, M) d\theta$$

In a variant, the invention provides for the method to make it possible to obtain 53 supplementary information corresponding to the a posteriori joint marginal distribution of the parameters of the local arterial input function for a tissue volume in question, such that:

$$p(\Theta_a \mid D, M) = \int_{\Theta \setminus \Theta_a} p(\Theta \mid D, M) d(\Theta \setminus \Theta_a)$$

The invention thus makes it possible to obtain for example a "mean" arterial input function $C_a(t, \widehat{\Theta_a})$ under the quadratic loss function $L(\Theta_a - \widehat{\Theta_a}^Q) = \|\Theta_a - \widehat{\Theta_a}^Q\|^2$ of joint parameters:

$$\hat{\Theta}_a^Q = \int_{\Theta_a} \Theta_a \cdot p(\Theta_a \mid D, M) d\Theta_a$$

or "the most probable" arterial input function of parameters:

$$\hat{\Theta}_a^P = \underset{\Theta_a}{\operatorname{argmax}} p(\Theta_a \mid D, M)$$

In the same way, the invention provides a variant embodiment for which a method according to the invention comprises a step 54 for calculating a "mean" or "the most probable" complementary cumulative distribution function $R(t, \widehat{\Theta_R})$.

It is thus also possible to obtain supplementary information in the form of estimations of the theoretical concentration of the contrast agent by $C(t, \hat{\Theta})$.

According to one embodiment, the invention provides for these arterial input functions or estimated complementary cumulative distribution functions, "mean" or "most probable", to be able to be compared with the one or those obtained by the approaches prior to the invention or to those obtained from distinct arterial input function or complementary cumulative distribution function models for the purpose of enabling the most relevant models to be selected.

This because it may be advantageous to compare the estimated arterial input functions with the true arterial input function when the latter is known and attempt to minimise the difference between them by introducing more appropriate models if necessary.

In relation to FIG. 8, the invention also provides for the possibility that a method according to the invention may comprise one or more supplementary steps for obtaining 53a confidence intervals or even to obtain 53b bets on these intervals for the parameters of the arterial input functions. The same may apply for obtaining 54a confidence intervals or even for obtaining 54b bets on these intervals for the parameters of the complementary cumulative distribution functions.

The dimensions of the typical parametric and semi-parametric modes for the arterial input functions $C_a(t,\Theta_a)$ and the complementary cumulative distribution functions $R(t,\Theta_R)$ are sufficiently small to be able to be applied to methods of sampling or approximating the a posteriori joint distribution $p(\Theta|D,M)$ and a marginal posterior distribution such as Markov Chain Monte-Carlo methods or the variational Bayes methods.

The invention consequently makes it possible to obtain approximations of the required estimations for the parameters of interest.

According to a particular embodiment, the invention provides for the method described in relation to FIG. 8 and implemented by a processing unit 4 adapted accordingly to be able to quantify the goodness-of-fit of the constrained global perfusion model to the experimental data D through calculation 55 of the probability of these data given the model $$p(D \mid M) = \int_\Theta p(\Theta \mid M) p(D \mid \Theta, M) d\Theta,$$

with $\Theta = \{\Theta_a, \Theta_R, \theta, S_0, \Theta_B\}$ in magnetic resonance imagining or $\Theta = (\Theta_a, \Theta_R, BF, \Theta_B)$ in computed tomography.

The calculation 55 of this quantity was not conceivable with the techniques of the art prior to the invention since, according to the latter, clearly determined global signal models are not available.

The invention provides for this quantity to make it possible to compare objectively several global perfusion models, possibly constrained, obtained from different sub-models for the arterial input function $Ca(t, \Theta_a)$ and/or different sub-models for the complementary cumulative distribution function $R(t, \Theta_R)$ and/or different supplementary constraints $\Psi(\Theta_a)=0$ as described previously.

Thus the invention provides for the method to be able to be implemented by the processing unit by successive iterations using distinct constrained global perfusion models. The processing unit can keep the result of the calculation 55 for each model used. The invention makes it possible to select in the end the best global perfusion model. This model is the one for Which the probability of the perfusion signals, given the model, is the greatest on average over all the voxels of interest.

In a variant, the invention provides for the method to be able to comprise steps 56a, 56b and 56c in order to choose, during an iteration, respectively a sub-model $C_a(t,\Theta_a)$, a sub-model $R(t,\Theta_R)$, or even a constraint $\Psi(\Theta_a)=0$ from a plurality and thus adjust 57 a global perfusion model. This selection can be carried out manually by a user 6 by means of parameters 16 or automatically by the method itself. Through an iterative process and successive tests, it becomes possible by virtue of the invention to progress in the modelling and the understanding of the perfusion phenomena and in the end to identify and validate the best models according to the patient, the pathologies, types of tissues, etc.

By way of example of application of the invention, we can cite the main steps of implementation of the invention by means of an adapted perfusion imaging analysis system such as the one described in FIG. 1 or 2:

opening of a patient case or taking into account sequences of images by the processing unit 4 (or processing 7) for selecting sequences of images of interest—in particular, selection of the perfusion images I1 to In over the course of time from which the perfusion signals S(t) are obtained for each voxel, as illustrated in FIG. 5a;

predisplay, by means of a human-machine interface 5, of the images to enable a user 6 to identify slices or areas of interest;

joint estimation by the processing unit 4 of the haemodynamic parameters 14, such as $\widehat{CBF}$ or $\widehat{MTT}$, for an organ such as the human-brain and delivery of the said parameters 14 to the human-machine interface 5 so that the latter in the end presents in the form of maps where the intensity or colour of each pixel depends on the value calculated, for example linearly; this step may also include the delivery of other estimated quantities such as confidence intervals, bets, or other complementary information associated with the parameters of the global perfusion model;

display of said maps in order to restore the content thereof to the user 6;

thresholding and filtering under the pulse 16 of the user 6 in order to keep only a region worthy of interest and/or to eliminate certain aberrations;

assisted selection of the said pathological area of interest by the user, characterised by an abnormality of the distribution of one or more haemodynamic parameters 14;

estimation, by the processing unit 4, of the volume of the abnormally perfused tissue area and optionally certain quantities such as the ratio of the volumes of the injured and abnormally perfused areas, on which a practitioner will be able to put the finishing touches to his diagnosis and his therapeutic decision making (e.g. intravenous thrombolysis in order to resorb a blood clot for example).

FIGS. 9 to 17 illustrate a display mode in the form of maps, of the haemodynamic parameters 14 estimated in accordance with the invention or even standard deviations or probabilities associated therewith.

Thus, for a human brain analysed by means of nuclear magnetic resonance imaging, FIG. 9 makes it possible to view an estimation of the cerebral blood volumes CBV. Such a map reveals a probable ischemic zone 80. This is because it is possible to find, by means of an adapted interface 6, an appreciable increase in the parameter CBV in the territory of the right posterior cerebral artery compared with the contralateral hemisphere. A vasodilation following ischemia may be revealed by reading the map as illustrated in FIG. 9.

Figure 12:
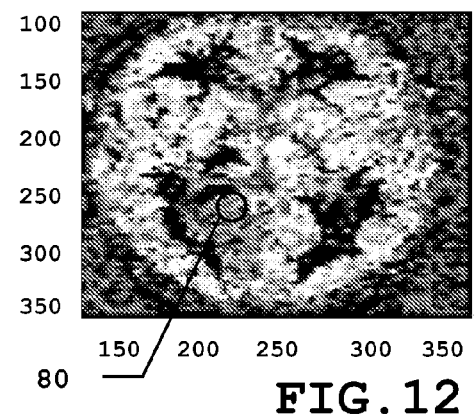

FIG. 12 describes a map relating to the estimation of the parameter a of a "tri-gamma" arterial input function model with 12 parameters in accordance with the invention. An appreciable decrease in a in the territory 80 of the right posterior cerebral artery can be found compared with the contralateral hemisphere. This information makes it possible to note a relative reduction in the quantity of contrast agent during circulation compared with the quantity during recirculation. This information is not available with the techniques according to the art prior to the invention.

Figure 13:
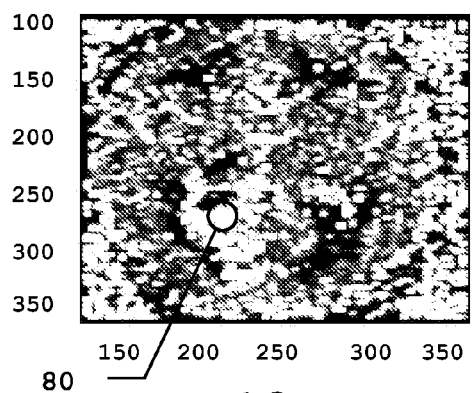

FIG. 13 describes a map relating to the estimation of the parameter $\beta_2$ of the "tri-gamma" arterial input function model with 12 parameters according to the invention. By analysing the map, an appreciable increase in $\beta_2$ can be found in the territory 80 of the right posterior cerebral artery compared with the contralateral hemisphere. This information is not available with the techniques according to the art prior to the invention.

Figure 14:
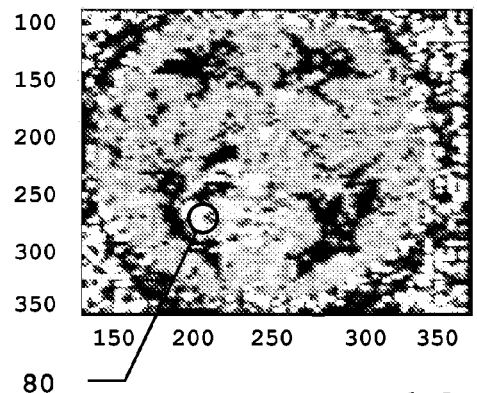

FIG. 14 describes a map relating to the estimation of the parameter $t_1$ of the "tri-gamma" arterial input function model with 12 parameters according to the invention. By analysing the map, an appreciable increase in $t_1$ can be found in the territory 80 of the right posterior cerebral artery compared with the contralateral hemisphere. This information is not available with the techniques according to the art prior to the invention.

Figure 10:
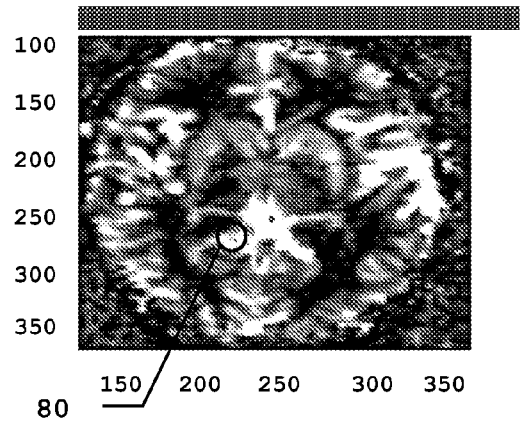
FIG. 10 illustrates a map relating to the estimation of the cerebral blood flows in the case of cerebral ischemia. By analysing the map, a slight decrease in the parameter CBF in the territory of the right posterior cerebral artery can be noted compared with the contralateral hemisphere following ischemia.
Figure 15:
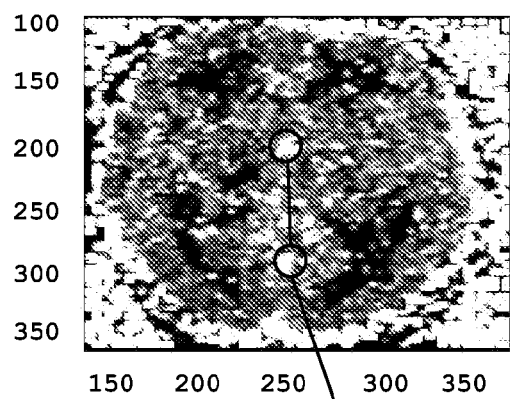

FIG. 15 describes a map relating to the estimation of the standard deviation of the cerebral blood flows $\sigma_{CBF}$ estimated from the "tri-gamma" arterial input function with twelve parameters according to the invention. By analysing the map it can be seen that the standard deviations are the highest in the zones 81 containing not tissue but arteries. The standard deviations are not higher in the ischemic area than in the contralateral area, reinforcing the estimation of the CBFs in this zone, as described by FIG. 10. This information is not available with the techniques according to the art prior to the invention.

Figure 11:
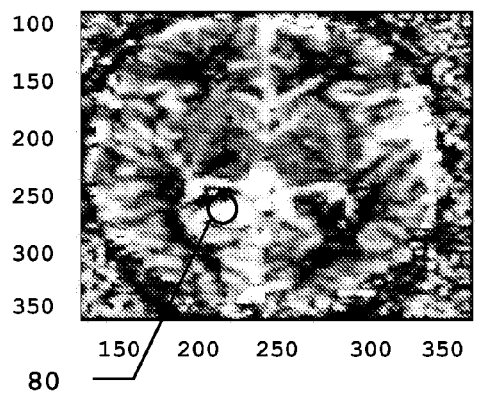
FIG. 11 illustrates a map relating to the estimation of the mean transit times MTT. By analysing the map, an appreciable increase in the MTTs can be found in the territory 80 of the right posterior cerebral artery compared with the contralateral hemisphere following ischemia.
Figure 16:
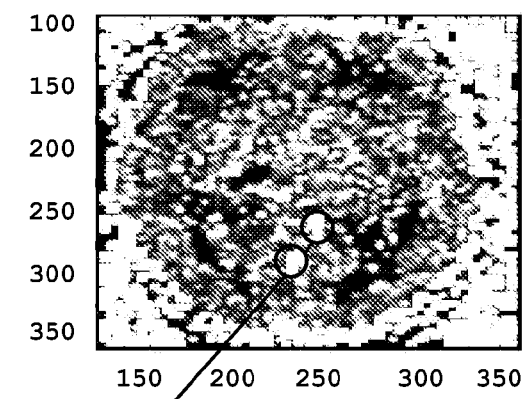

FIG. 16 describes a map relating to the estimation of the standard deviation of the estimated mean transit times $\sigma_{MTT}$ from the "corrected gamma integral" complementary cumulative distribution function model with two parameters according to the invention. It can be seen, by analysing the map, that the standard deviations are the highest in the zones 82 containing not tissue but arteries. It is a case precisely of a zone similar to those where the standard deviations of the cerebral blood flows are also the highest. The standard deviations are not higher in the ischemic area than in the contralateral area, reinforcing the estimation of the MTTs in this zone, an estimation as described by FIG. 11. This information is not available with the techniques according to the art prior to the invention.

Figure 17:
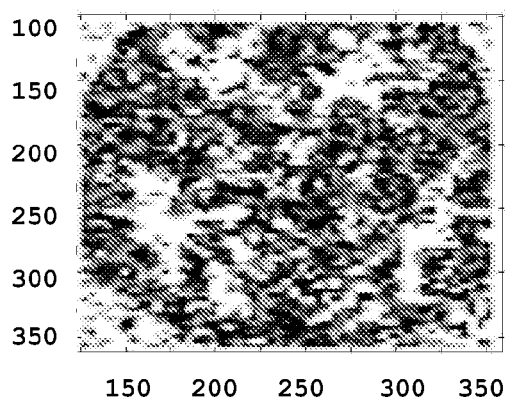

FIG. 17 describes a map relating to the estimation of the probability that the cerebral blood flow is in the confidence interval $[\widehat{CBF} = \hat{\sigma}CBF, \widehat{CBF} + \hat{\sigma}CHF]$ under the "tri-gamma" arterial input function model with twelve parameters according to the invention. It can be seen by analysing the map that, apart from aberrant adjustments, the probabilities are centred around 0.68. It is a value that one is entitled to expect if the a posteriori probability distribution of CBF is a normal law.

Figure 1:
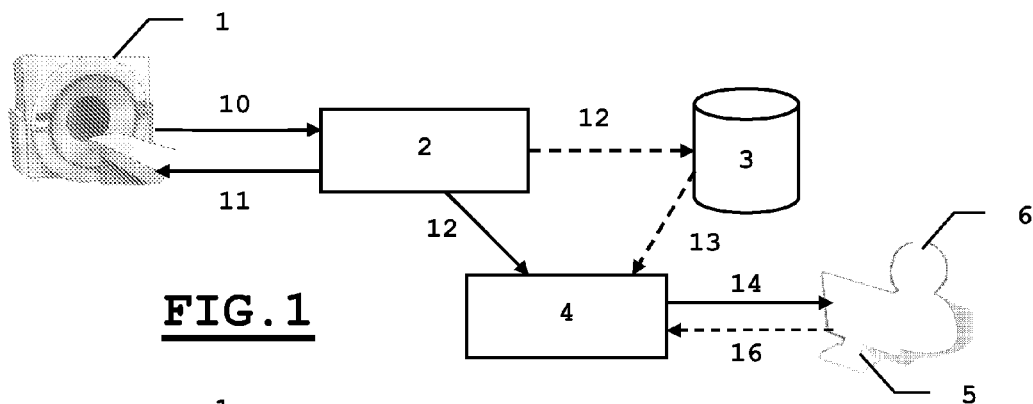
Figure 2:
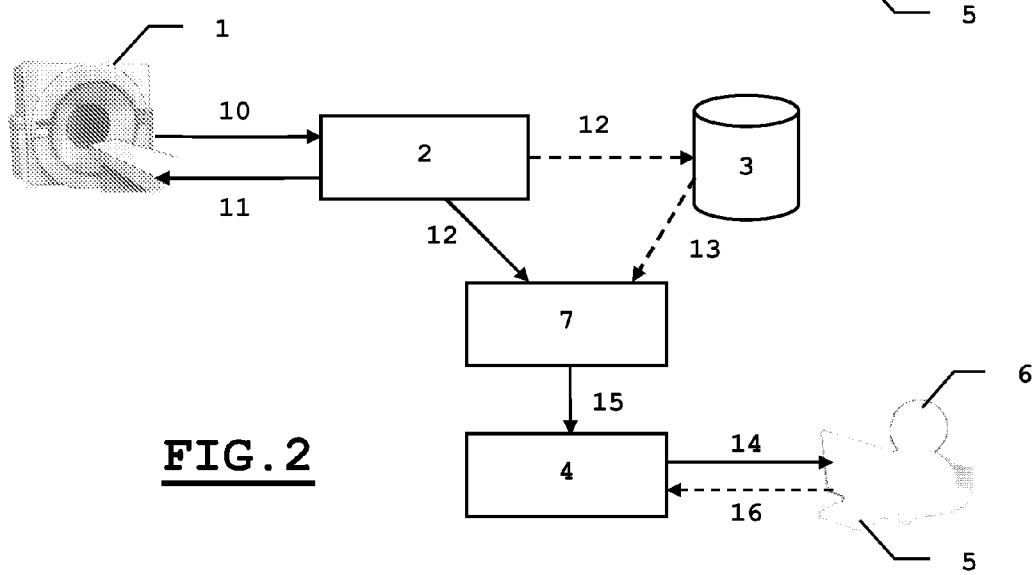
Figure 3:
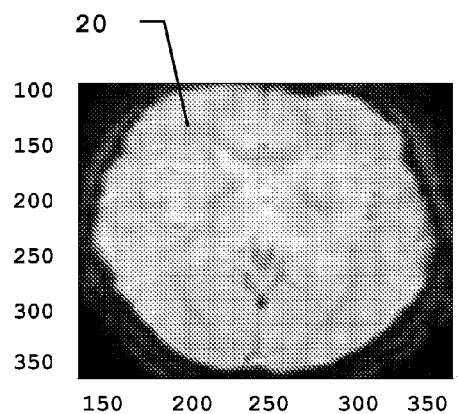
Figure 4:
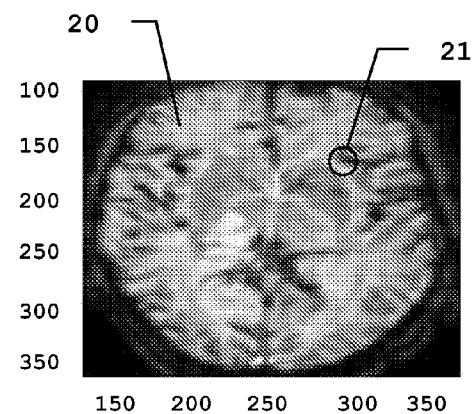
Figure 5A:
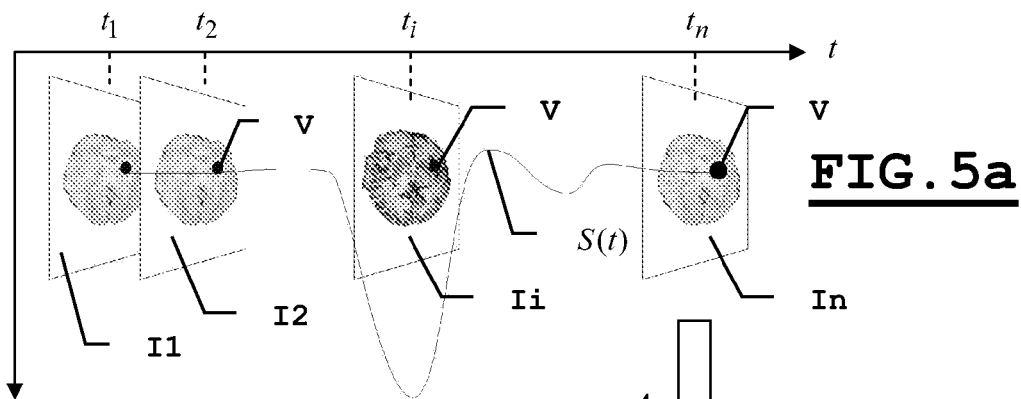
Figure 5B:
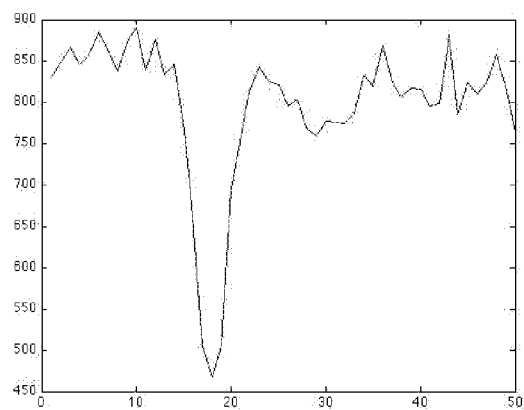
Figure 6:
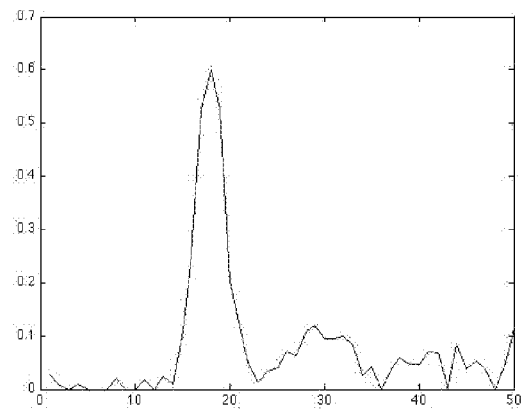
Figure 7:
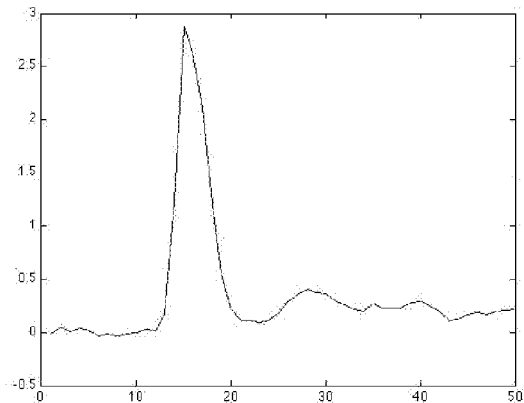
Figure 8:
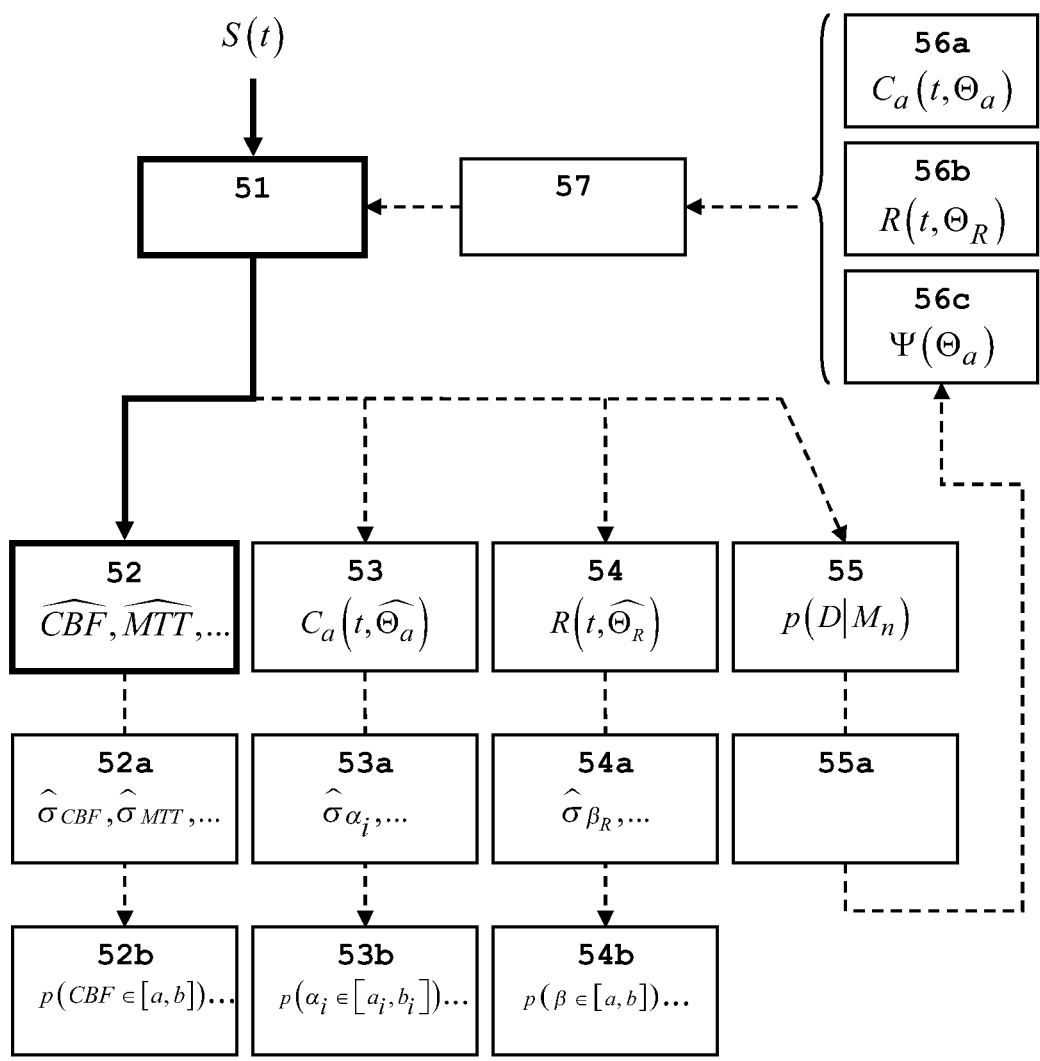
Figure 9:
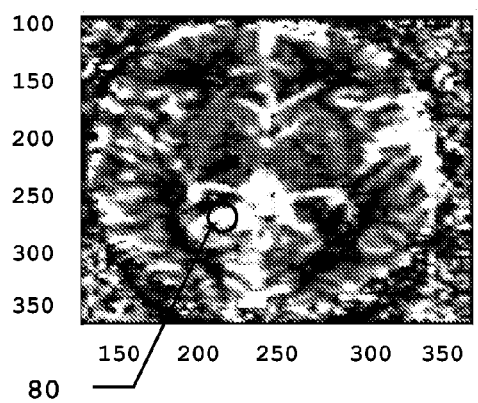

By means of the maps presented above, the invention makes available to a user a whole range of useful information, information that could not be available by means of the techniques known from the prior art. This making available is made possible by an adaptation of the processing unit 4 according to FIGS. 1 and 2 in that its means for communicating with the outside world of the unit 4 are able to deliver estimated parameters 14 according to a format appropriate to a human-machine interface 5 able to restore to a user 6 the said estimated parameters in the form for example of maps as illustrated by FIGS. 9 to 17.

We can also remark that the invention makes it possible to eliminate steps necessary according to the techniques of the art prior to the invention. Among various steps we can cite the elimination of:

the manual or automatic selection or determination of a global arterial input function or of local arterial input functions;

the implementation by the processing unit of a deconvolution algorithm of the standard perfusion model $C(t) = \eta \cdot BF \cdot C_a(t) \otimes R(t)$ for each voxel, on the basis of the selected arterial input function or functions, in order to obtain an estimation of $BF \cdot R(t)$.

We can also remark that, according to the invention, the processing unit is adapted to implement a joint estimation algorithm for the parameters of the global perfusion model instead of a deconvolution algorithm in accordance with the prior techniques.

By virtue of the invention, the items of information delivered are more numerous and accurate. The information available to a researcher or practitioner are thus of such a nature as to increase their confidence in the determination of a diagnosis and a therapeutic decision.

In order to improve the performance of the system according to the invention, the latter provides for the processing unit 4 to be able to provide it with means for putting in parallel calculations on the voxels of the image for which the estimation of the parameters is required. Such a processing unit may comprise means such as graphical microprocessors (graphical processor units (GPUs)) or use calculation clusters. In a variant such a processing unit may use programmed means such as parallel Monte-Carlo methods. In a variant, the processing unit according to the invention can rely on remote computing means. The computing times can thus be considerably reduced. In addition, a processing unit according to the invention can comprise means for storing one or more global perfusion models or a plurality of arterial input function sub-models or complementary cumulative distribution function sub-models of the transit time or a plurality of constraints based on the parameters of the said arterial input function sub-models. In a variant such a processing unit may allow loading of such global perfusion models, possibly constrained, or sub-models or even constraints by means of its means for communicating with the outside world. The latter may be able to implement a cabled or remote communication according to techniques known from the prior art.

The invention has been described and illustrated in the field of dynamic susceptibility contrast magnetic resonance imaging (DSC-MRI). The invention should not be limited solely to this example application but can also apply to other medical technologies such as perfusion imaging by computed tomography in particular.

The invention claimed is:

1. A method for estimating and presenting a representation of one or more haemodynamic perfusion parameters of an elementary volume, referred to as a voxel, of an organ, said method being implemented by a processing unit of a perfusion imaging analysis system, and comprising:
   obtaining perfusion signals S(t) derived from images of the organ;
   estimating the haemodynamic parameter or parameters using a joint estimation of the parameters $\Theta$ of a global perfusion model comprising:
      a first relationship between the perfusion signal S(t) and a concentration C(t) of a contrast agent circulating in said voxel over a time t,
      a second relationship between the concentration C(t) of a contrast agent, the blood flow BF, a parametric or semiparametric model $C_a(t,\Theta_a)$ of an arterial input function and a parametric or semiparametric model $R(t,\Theta_R)$ of a complementary cumulative distribution function of the transit time in the voxel, $\Theta_a$ and $\Theta_R$ being respectively the parameters of the models $C_a(t,\Theta_a)$ and $R(t,\Theta_R)$, and
      a third relationship $\Psi(\Theta a)=0$ between the parameters $\Theta a$ of the model of the arterial input function $Ca(t\Theta_a)$; and
   displaying a graphical representation of the estimated value or values for the parameter or parameters on a human-machine interface for evaluation by a user.

2. A method according to claim 1, wherein:
the perfusion signal S(t) is obtained from digital images delivered by a magnetic resonance perfusion imaging apparatus;

the first relationship of the global perfusion model is expressed by $S(t)=S_0 e^{-k \cdot TE \cdot C(t)}$ where $S_0$ is the mean intensity of the signal before the arrival of the contrast agent in the voxel, TE is an echo time and k is a non-zero constant; and the second relationship of the global perfusion model is expressed by $C(t)=\eta \cdot BF \cdot C_a(t,\Theta_a) \otimes R(t,\Theta_R)$ where $\otimes$ designates the convolution product, $\eta$ is a non-zero constant and BF is the blood flow in the voxel.

3. A method according to claim 1, wherein:
the perfusion signal S(t) is obtained from digital images delivered by a computed tomography perfusion imaging apparatus;

the first relationship of the global perfusion model is a proportionality equation $S(t)=\alpha \cdot C(t)$ where $\alpha$ where is a non-zero constant; and the second relationship of the global perfusion model is expressed by $C(t)=\eta \cdot BF \cdot C_a(t,\Theta_a) \otimes R(t,\Theta_R)$ where $\otimes$ designates the convolution product, $\eta$ is a non-zero constant and BF is the blood flow in the voxel.

4. A method according to claim 1, comprising successive iterations for a plurality of voxels of the organ.

5. A method according to claim 1, where the joint estimation of the parameters $\Theta$ of the global perfusion model used by the processing unit is implemented by means of the Bayes method or the method of Maximum Likelihood methods or the method non-linear least squares.

6. A method according to claim 1, further including far quantifying the goodness-of-fit of the global perfusion model to experimental perfusion data $D=[S(t_1), \ldots, S(t_N)]$ by a calculation of a probability $$p(D \mid M) = \int_\Theta p(\Theta \mid M) p(D \mid \Theta, M) d\Theta$$

of these data given said model.

7. A method according to claim 6, further comprising iteratively implementing the method by the processing unit for each global perfusion model of the plurality of models.

8. A method according to claim 7, wherein the estimated parameters according to the perfusion model, whose probability is the greatest, are delivered.

9. A method according to claim 1, further comprising choosing a global perfusion model from a plurality of models.

10. A method according to claim 1, wherein the model $Ca(t,\Theta_a)$ of an arterial input function is a so-called "tri-gamma" model with twelve parameters defined by:

$$\begin{cases} C_a(t, \Theta_a) = \frac{a(t-t_0)^{\alpha_0-1} e^{-(t-t_0)/\beta_0}}{\beta_0^{\alpha_0} \Gamma(\alpha_0)} + \frac{b(t-t_1)^{\alpha_1-1} e^{-(t-t_1)/\beta_1}}{\beta_1^{\alpha_1} \Gamma(\alpha_1)} + \\ \frac{c(t-t_2)^{\alpha_2-1} e^{-(t-t_2)/\beta_2}}{\beta_2^{\alpha_2} \Gamma(\alpha_2)} \\ \Theta_a = (a, b, c, \alpha_0, \beta_0, t_0, \alpha_1, \beta_1, t_1, \alpha_2, \beta_2, t_2) \\ \Gamma(\,): \textit{Euler} \text{ gamma function} \end{cases}$$

11. A method according to claim 1, wherein the model $R(t,\Theta_R)$ of a complementary cumulative distribution function of the transit time in the voxel is a so-called "corrected integral gamma" model with two parameters defined by:

$$\begin{cases} R(t, \Theta_R) = H(t) - \int_0^t h(\tau, MTT, \beta) d\tau \\ h(\tau, MTT, \beta) = \dfrac{t^{\frac{MTT}{\beta}-1} e^{-t/\beta}}{\beta^{\frac{MTT}{\beta}} \Gamma\left(\dfrac{MTT}{\beta}\right)} \quad MTT > 0, \beta > 0 \\ \Theta_R = (MTT, \beta) \\ H(\ ): \text{generalised Heaviside step function} \\ \Gamma(\ ): \text{Euler gamma function} \end{cases}$$

12. A method according to claim 1, wherein the third relationship $\Psi(\Theta a)=0$ of the global perfusion model is expressed as $$\int_0^{+\infty} C_{ca}(t, \Theta_{ca}) dt = C_0$$

where $C_0$ is a non-zero arbitrary constant identical for any voxel of interest.

13. A method according to claim 1, wherein the third relationship of the global perfusion model $\Psi(\Theta a)=0$ is expressed as $$\int_0^{+\infty} C_{ca}(t, \Theta_{ca}) dt = C_0$$

where $C_{ca}(t,\Theta_{ca})$ is a component of the model $C_a(t,\Theta_a)$ modelling the concentration of the contrast agent during its first pass and $C_0$ is a non-zero arbitrary constant identical for any voxel of interest.

14. A method according to claim 1, further comprising calculating complementary information in the form of an estimated arterial input function $C_a(t, \widehat{\Theta_a})$.

15. A method according to claim 14, further comprising delivering the complementary information to the human-machine interface for display to the user.

16. A method according to claim 1, further comprising calculating complementary information in the form of an estimated complementary cumulative distribution function $R(t, \widehat{\Theta_R})$.

17. A method according to claim 1, further comprising calculating complementary information in the form of a confidence interval associated with a parameter of the global perfusion model.

18. A method according to claim 1, further comprising calculating complementary information in the form of a bet associated with a parameter of the global perfusion model.

19. The method of claim 1, wherein the graphical representation comprises a map of the organ.

20. A processing unit comprising a storage device, an interface for communicating with the outside world and a processor, wherein:
the interface is configured to receive from the outside world a signal S(t) obtained by perfusion imaging;
the storage device stores a global perfusion model, said model comprising:
a first relationship between the perfusion signal S(t) and a concentration C(t) of a contrast agent circulating in a voxel over the course of time t,
a second relationship between the blood flow BF in the voxel, the concentration C(t), a parametric or semiparametric model $C_a(t,\Theta_a)$ of an arterial input function and a parametric or semiparametric model R(t, $\Theta_R$) of a complementary cumulative distribution function of the transit time in the voxel, $\Theta_a$ and $\Theta_R$ being respectively the parameters of the models, and
a third relationship $\Psi(\Theta a)=0$ between the parameters $\Theta a$ of the model of the arterial input function $C_a(t\Theta_a)$; and
the processor is configured to implement a method for estimating haemodynamic perfusion parameters according to claim 1.

21. A processing unit according to claim 20, wherein the interface delivers one or more estimated parameters according to an appropriate format to a human-machine interface configured to display said estimated parameters to a user.

22. A perfusion imaging analysis system comprising a processing unit according to claim 20 and a human-machine interface configured to display to a user one or more parameters estimated by said processing unit.

23. A processing unit comprising a storage device, an interface for communicating with the outside world and a processor, wherein:
the interface is configured to receive digital perfusion images from the outside world;
the storage device stores a global perfusion model, said model comprising:
a first relationship between a perfusion signal S(t) and a concentration C(t) of a contrast agent circulating in a voxel in the course of time t,
a second relationship between the concentration C(t), the blood flow BF, a parametric or semiparametric model $C_a(t,\Theta_a)$ of an arterial input function and a parametric or semiparametric model R(t,$\Theta_R$) of a complementary cumulative distribution function of the transit time in the voxel, $\Theta_a$ and $\Theta_R$ being respectively the parameters of the models, and
a third relationship $\Psi(\Theta a)=0$ between the parameters $\Theta a$ of the model of the arterial input function $Ca(t\Theta_a)$; and
the processor is configured to determine a perfusion signal S(t) from perfusion images received and to implement a method for estimating one or several haemodynamic perfusion parameters according to claim 1.

* * * * *